United States Patent
Taerum

(10) Patent No.: US 12,278,009 B2
(45) Date of Patent: Apr. 15, 2025

(54) SYSTEMS AND METHODS FOR MEDICAL IMAGE PRESENTATION IN MULTIPLE CONTEXTS

(71) Applicant: Arterys Inc., San Francisco, CA (US)

(72) Inventor: Torin Arni Taerum, Cochrane (CA)

(73) Assignee: Arterys Inc., San Francisco, CA (US)

( * ) Notice: Subject to any disclaimer, the term of this patent is extended or adjusted under 35 U.S.C. 154(b) by 386 days.

(21) Appl. No.: 17/850,805

(22) Filed: Jun. 27, 2022

(65) Prior Publication Data

US 2022/0415479 A1 Dec. 29, 2022

Related U.S. Application Data

(60) Provisional application No. 63/216,218, filed on Jun. 29, 2021.

(51) Int. Cl.
*G16H 30/20* (2018.01)
*G06F 40/169* (2020.01)

(52) U.S. Cl.
CPC .......... *G16H 30/20* (2018.01); *G06F 40/169* (2020.01)

(58) Field of Classification Search
USPC ....................................................... 382/184
See application file for complete search history.

(56) References Cited

U.S. PATENT DOCUMENTS

| | | | |
|---|---|---|---|
| 2005/0065424 A1* | 3/2005 | Shah | G16H 40/63 600/407 |
| 2007/0127791 A1 | 6/2007 | Ernvik et al. | |
| 2013/0083068 A1 | 4/2013 | Lethers et al. | |
| 2014/0164948 A1* | 6/2014 | Joo | H04L 12/1813 715/752 |

FOREIGN PATENT DOCUMENTS

EP 3790023 A1 3/2021

OTHER PUBLICATIONS

Huang et al., "Web-based Remote Collaboration over Medical Image Using Web Services", Information *Infrastructure Symposium*, IEEE, Piscataway, NJ, USA, Jun. 23, 2009, pp. 1-8. (8 pages).
International Search Report and Written Opinion, mailed Oct. 10, 2022, for International Application No. PCT/US2022/035155, 16 pages.

* cited by examiner

*Primary Examiner* — Jacky X Zheng
(74) *Attorney, Agent, or Firm* — Seed Intellectual Property Law Group LLP

(57) ABSTRACT

This disclosure relates to a system that synchronizes the presentation of medical images in multiple contexts and methods thereof. The system includes a variety of contexts that display medical images, and the contexts are connected by communication channels. When a user edits or otherwise interacts with one of the contexts, a message is sent to other contexts via the communication channels, and the other contexts can adjust their presentation of medical images to achieve synchronization.

16 Claims, 4 Drawing Sheets

SYSTEMS AND METHODS FOR MEDICAL IMAGE PRESENTATION IN MULTIPLE CONTEXTS

CROSS-REFERENCE TO RELATED APPLICATIONS

This application claims the benefit of priority to U.S. Provisional Application No. 63/216,218, filed Jun. 29, 2021, which application is hereby incorporated by reference in its entirety.

TECHNICAL FIELD

The present disclosure generally relates to medical imaging and particularly rendering and presenting medical imaging in a variety of contexts.

BACKGROUND

Medical images usually include two-dimensional images, three-dimensional images, or reconstructed fused images generated through imaging equipment utilizing modern nuclear medicine techniques, for example, positron emission tomography (PET), computed tomography (CT), magnetic resonance imaging (MRI), functional MRI (fMRI), X-ray, mammography, tomosynthesis, ultrasound or other modalities. Medical images may be presented to health professionals and patients in the course of rendering diagnosis, treatment, or other health care.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

Figure 1:
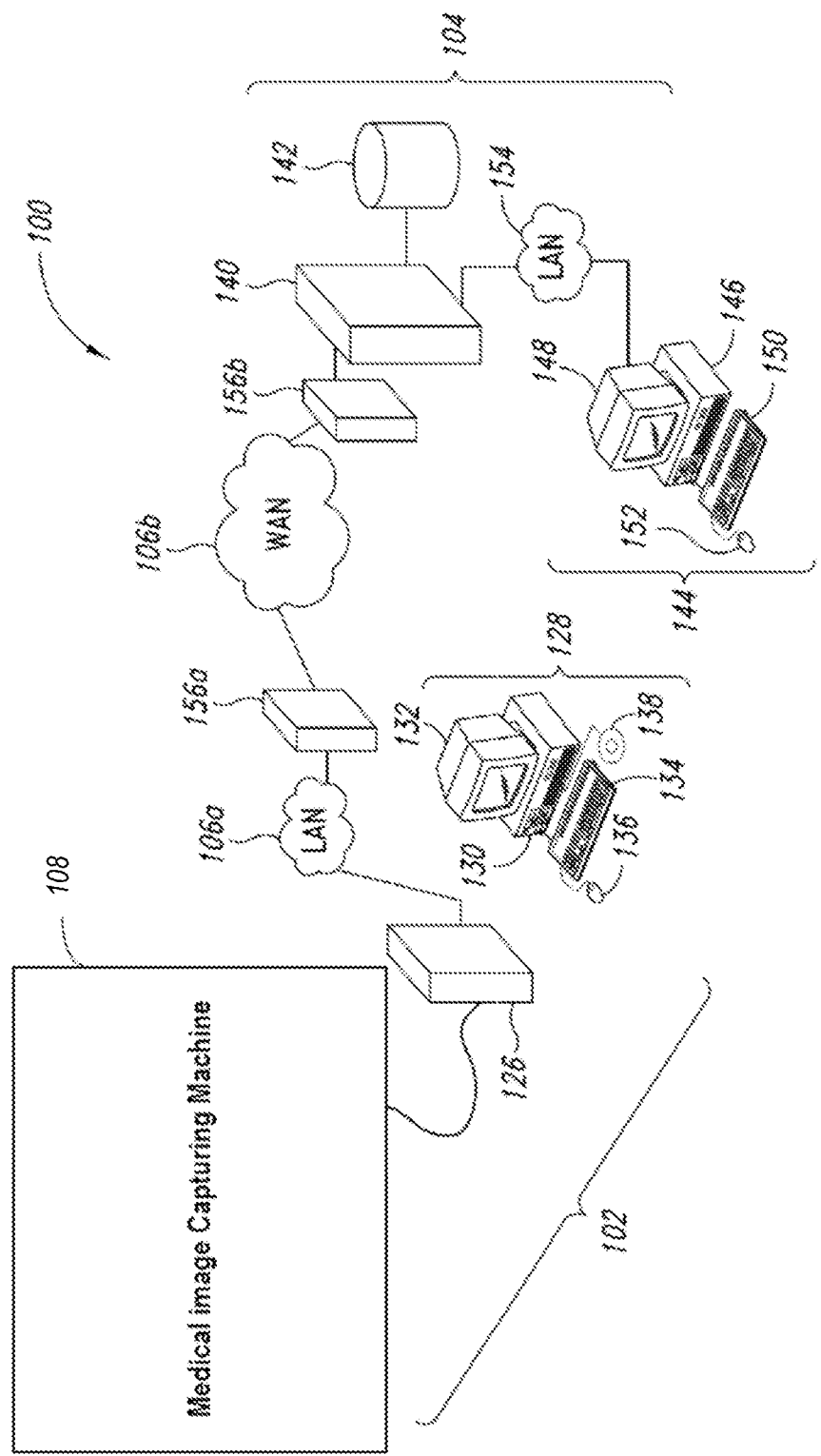
FIG. 1 is a schematic view of a networked environment where the presently disclosed technology is implemented, according to some embodiments.

Medical images featuring the same or related organ, tissue, or other parts of a patient are often displayed in many contexts. When a user edits a medical image in one of the contexts, such as adjusting the aspect ratio of the medical image or adding annotative labels, shapes, or texts to the medical image, the change is not automatically reflected in other contexts. Embodiments of the presently disclosed technology are directed to synchronizing or otherwise coordinating the presentation of medical images in various contexts.

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks and the environment, have not been shown or described in order to avoid unnecessarily obscuring descriptions of the embodiments. Additionally, the various embodiments may be methods, systems, media, or devices. Accordingly, the various embodiments may combine software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

References to the term "set" (e.g., "a set of items"), as used herein, unless otherwise noted or contradicted by context, is to be construed as a nonempty collection comprising one or more members or instances.

References to the term "subset" (e.g., "a subset of the set of items"), as used herein, unless otherwise noted or contradicted by context, is to be construed as a nonempty collection comprising one or more members or instances of a set or plurality of members or instances.

Moreover, the term "subset," as used herein, refers to a proper subset, which is a collection of one or more members or instances that are collectively smaller in number than the set or plurality of which the subset is drawn. For instance, a subset of a set of ten items will have less than ten items and at least one item.

FIG. 1 shows a networked environment 100 according to some embodiments, in which one or more medical image acquisition systems (one shown) 102 are communicatively coupled to at least one medical image processing and display system 104 via one or more networks 106a, 106b (two shown, collectively 106).

The medical image acquisition system 102 is typically located at a clinical facility, for instance a hospital or dedicated medical imaging center. Examples of such medical acquisition systems include, but are not limited to: radiological imaging systems, medical x-ray imaging systems, mammography imaging systems, full-field digital mammography (FFDM) imaging systems, magnetic resonance imaging (MM) imaging systems, computerized tomography (CT) or computed axial tomography (CAT) imaging systems, ultrasound imaging systems, positron emission tomography (PET) imaging systems, single-photon emission computed tomography (SPECT or SPET) imaging systems, optical imaging systems and an optical coherence tomography (OCT) imaging systems. Various techniques and structures, as explained herein, can allow the image processing and display system 104 to be remotely located from the medical image acquisition system 102. The image processing and display system 104 may, for example, be located in another building, city, state, province, or even country.

The medical image acquisition system 102 may, for example, include a medical image capturing machine 108, a computer system 110, and a medical image capturing operator's system 128. The medical image capturing machine 108 typically includes, or is communicatively coupled to, a processor-based control system 126 used to control the medical image capturing machine 108. The processor-based control system 126 may include one or more processors, non-transitory computer- or processor-readable memory, drive circuitry and/or interface components to interface with the medical image capturing machine 108. The processor-based control system 126 may, in some implementations, also perform some preprocessing on data resulting from the medical imaging operation.

An operator's system 128 may include a computer system 130, monitor or display 132, keypad and/or keyboard 134, and/or a cursor control device such as a mouse 136, joystick, trackpad, trackball or the like. The operator's system 128 may include or read computer- or processor-executable instructions from one or more non-transitory computer- or processor-readable medium, for instance media 138 such as flash memory, or a magnetic or optical disk. The operator's system 128 may allow a technician to operate the medical image capturing machine 108 to capture or otherwise obtain medical image data from a patient. Various techniques, structures and features described herein may allow medical image capturing machine 108 operation by a technician without requiring the presence of a clinician or physician.

The image processing and display system 104 may include one or more servers to handle incoming requests and responses, and one or more rendering or image processing and display computers 140. The server(s) may, for example take the form of one or more server computers, workstation computers, supercomputers, or personal computers, executing server software or instructions. The one or more rendering or image processing and display computers 140 may take the form of one or more computers, workstation computers, supercomputers, or personal computers, executing image processing and/or analysis software or instructions. The one or more rendering or image processing and display computers 140 will typically employ one, and preferably multiple, graphical processing units (GPUs) or GPU cores.

The image processing and display system 104 may include one or more non-transitory computer-readable medium 142 (e.g., solid state hard drives, magnetic or optical hard drives, RAID, RAM, or Flash) that stores processor-executable instructions, data or other information. The image processing and display system 104 may include one or more image processing and display operator's systems 144. The image processing and display operator's system 144 may include a computer system 146, monitor or display 148, keypad or keyboard 150, or a cursor control device such as a mouse 152, joystick, trackpad, trackball or the like. The image processing and display operator's system 144 may be communicatively coupled to the rendering or image processing and display computer(s) 140 via one or more networks, for instance a LAN 154. While many image processing techniques and analysis may be fully automated, the image processing and display operator's system allows a technician to perform certain image processing or analysis operations on medical image data.

While illustrated as a single non-transitory computer- or processor-readable storage medium 142, in many implementations the non-transitory computer- or processor-readable storage medium 142 may constitute a plurality of non-transitory storage media. The plurality of non-transitory storage media may be commonly located at a common location, or distributed at a variety of remote locations. The computer- or processor-readable storage medium 142 may be co-located with the image processing and display system 104, for example, in the same room, building or facility. Alternatively, the computer- or processor-readable storage medium 142 may be located remotely from the image processing and display system 104, for example, in a different facility, city, state or country. Electronic or digital information, files or records or other collections of information may be stored at specific locations in non-transitory computer- or processor-readable media 142, thus are logically addressable portions of such media, which may or may not be contiguous.

As noted above, the image processing and display system 104 may be remotely located from the medical image acquisition system 102. The medical image capturing machine 108 and the image processing and display system 104 are capable of communications, for example via one or more communication connections, for example local area networks (LANs) 106a and Wide Area Networks (WANs) 106b. The networks 106 may, for instance include packet switched communications networks, such as the Internet, Worldwide Web portion of the Internet, extranets, and/or intranets. The networks 106 may take the form of various other types of telecommunications networks, such as cellular phone and data networks, and plain old telephone system (POTS) networks. The type of communications infrastructure should not be considered limiting.

While not illustrated, the communications network may include one or more additional networking devices. The networking devices may take any of a large variety of forms, including servers, routers, network switches, bridges, and/or modems (e.g., DSL modem, cable modem), etc.

In the depicted exemplary networked environment 100, the connections 106 may comprise one or more computer networks, one or more wired or wireless networks, satellite transmission media, one or more cellular networks, or some combination thereof. The connections 106 may include a publicly accessible network of linked networks, possibly operated by various distinct parties, such as the Internet. The connections 106 may include other network types, such as one or more private networks (e.g., corporate or university networks that are wholly or partially inaccessible to non-privileged users), and may include combinations thereof, such that (for example) one or more of the private networks have access to or from one or more of the public networks. Furthermore, the connections 106 may include various types of wired or wireless networks in various situations, including satellite transmission. In addition, the connections 106 may include one or more communication interfaces to individual entities in the networked environment 100, various other mobile devices, computing devices and media devices, including but not limited to, radio frequency (RF) transceivers, cellular communication interfaces and antennas, USB interfaces, ports and connections (e.g., USB Type-A, USB Type-B, USB Type-C (or USB-C), USB mini A, USB mini B, USB micro A, USB micro C), other RF transceivers (e.g., infrared transceivers, Zigbee® network connection interfaces based on the IEEE 802.15.4 specification, Z-Wave® connection interfaces, wireless Ethernet ("Wi-Fi") interfaces, short range wireless (e.g., Bluetooth®) interfaces and the like.

While FIG. 1 illustrates a representative networked environment 100, typical networked environments may include many additional medical image acquisition systems, image processing and display systems 104, computer systems, and/or entities. The concepts taught herein may be employed in a similar fashion with more populated networked environments than that illustrated. For example, the entity that provides the image processing and display services can operate multiple systems and provide image processing and display systems 104 which may include two, three or even hundreds of rendering or image processing and display computers 140 and operators' systems 144.

Figure 2:
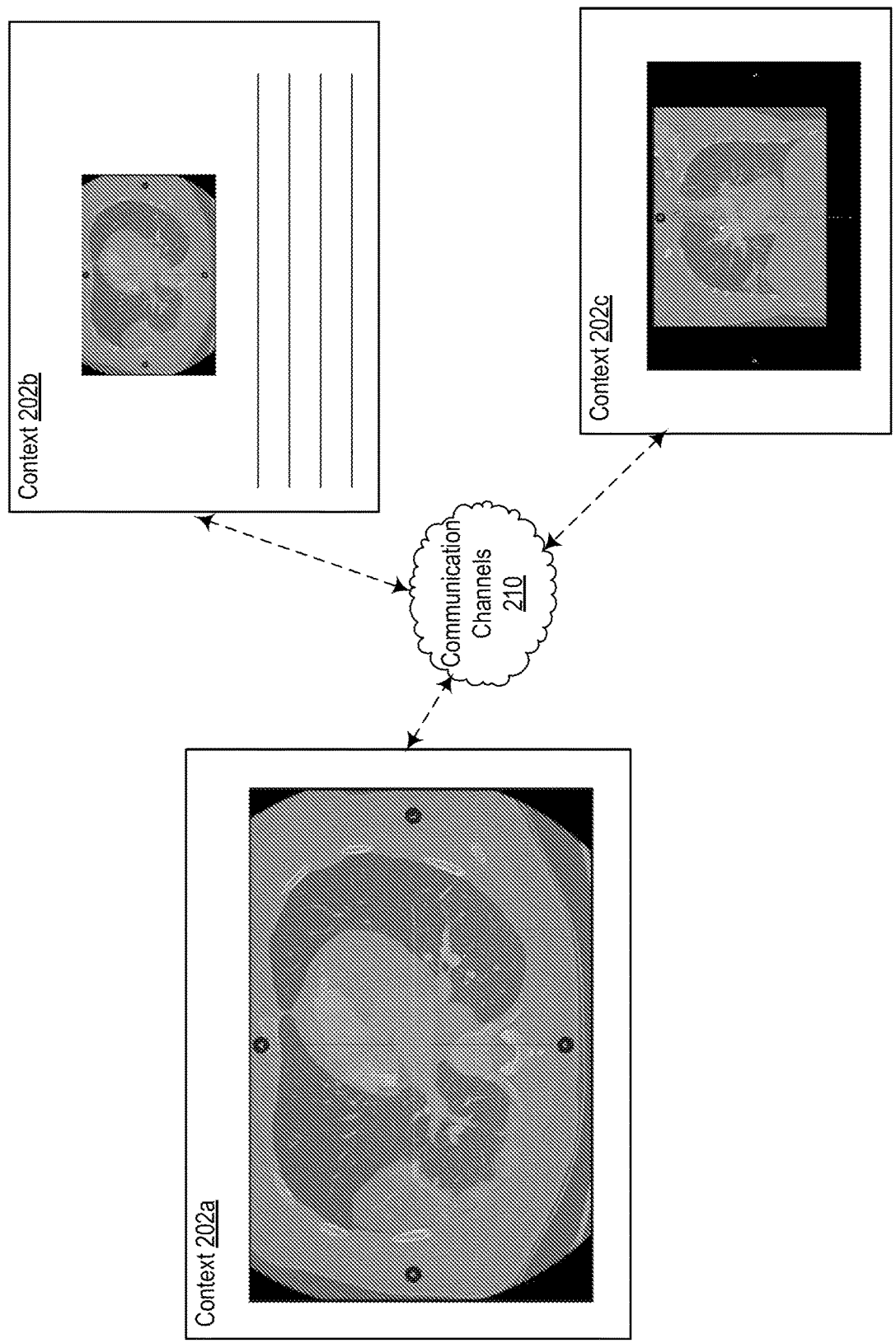
FIG. 2 is an illustration of the structure and function of the presently disclosed technology, according to some embodiments.

FIG. 2 illustrates an example of medical image presentation in multiple contexts, according to some embodiments. As illustrated, multiple contexts 202 containing medical image(s) are connected via communication channels 210. The contexts 202a-c can be displayed using the same software application or different applications. The application(s) can be the medical image processing and display system 104, and in some embodiments, the medical image acquisition system 102, or in some embodiments, part of the medical image processing and display system, or the medical image acquisition system. The application(s) can run on the same device or different devices connected by a local network or connected to the Internet. Illustratively, the contexts 202a-c can be different browser windows, different tabs (e.g., of a single browser window or different browser windows), different frames (e.g., of a single or different tabs, a single or different browser windows, combination of the same or the like).

The communication channels 210 can be implemented as software alone, or can also contain hardware components. For example, if the contexts 202a-c belong to multiple processes of the same software application or multiple software applications running on the same device, the communication channels 210 can be implemented as an object that sends and receives messages between processes. If the contexts 202a-c belong to processes running on multiple devices that are connected by a local network or connected to the Internet, the implementation of the communication channels 210 can include both software and hardware parts. The software part can include a "sender" end and a "receiver" end. The "sender" end can obtain the original message from a context, encode the message, divide the message into packets, encapsulate the packets, and transmit the packets over the local network or the Internet in accordance with applicable network protocols (e.g., TCP, UDP, IP, or the like). The "receiver" end can receive the packets containing the relevant information, decapsulate the packets, concatenate the packets to retrieve the message, decode the message, and send the message to the other contexts in the group of context 202a-c for further processing. The hardware part can include networking devices such as servers, routers, network switches, bridges, and/or modems (e.g., DSL modem, cable modem), etc.

In some embodiments, the contexts 202a-c display or otherwise present medical images featuring the same organ, tissue, or other parts of a patient, but the presentations can have different sizes, aspect ratios, pixel depths, orientations, timing, or the like. The medical images may feature the same origin, but represent views from different perspectives. For example, in FIG. 2, contexts 202a and 202b both include images featuring the side view of a pair of lungs, but context 202c includes a medical image featuring the top view of the same pair of lungs. The contexts can also contain elements other than medical images, such as annotative labels, shapes, or texts. For example, in FIG. 2, context 202b includes lines of annotative text under the medical image. As another example, medical images presented in different context are the same type of scan captured at different times (e.g., 1 month apart), and the views between two screens are synchronously modified by user input (e.g., so the user can easily see changes over time with consistent views).

In some embodiments, when one or more environmental characteristics of one of the contexts 202a-c connected by the communication channels 210 is updated, information regarding the update is communicated to the other contexts via the communication channels. Based on the information, one or more corresponding environmental characteristics of the other contexts can also be updated accordingly. The medical images and/or other elements in the other contexts can be displayed in accordance with the updated environmental characteristics. For example, in FIG. 2, if a user updates the aspect ratio of the medical image from 1:1 to 1:0.9 in context 202a, the update can be communicated to contexts 202b and 202c. Context 202b can update its medical image's aspect ratio from 1:1 to 1:0.9 according to the update in context 202a. Since the image in 202c is a top view of a pair of lungs but the images in contexts 202a and 202b are side views of the pair of lungs, context 202c may not update the aspect ratio of the image in it. As another example, medical images presented in different context are the same type of scan captured at different times (e.g., 1 month apart), and the views or other presentations from the different contexts are synchronously modified by user interactions (e.g., flagging, labeling, measuring, or the like) with one of the contexts, so that the user can easily see changes over time with consistent presentations.

In some embodiments, any context in the group of contexts 202a-c can communicate updated environmental characteristics to other contexts in the group via the communication channels 210, and any context can receive updated environmental characteristics and display the medical image(s) and, possibly, other elements in the context according to the update.

In some embodiments, the environmental characteristics can include attributes of annotative element(s), sizes, aspect ratios, pixel depths, colors, brightness, and orientations of the medical image(s), as well as other parameters of the medical image(s). In some embodiments, the environmental characteristics include the inclusion or omission of annotative elements such as labels, shapes, or texts, as well as their attributes, such as colors, sizes, orientations, locations, content, or the like.

Figure 3:
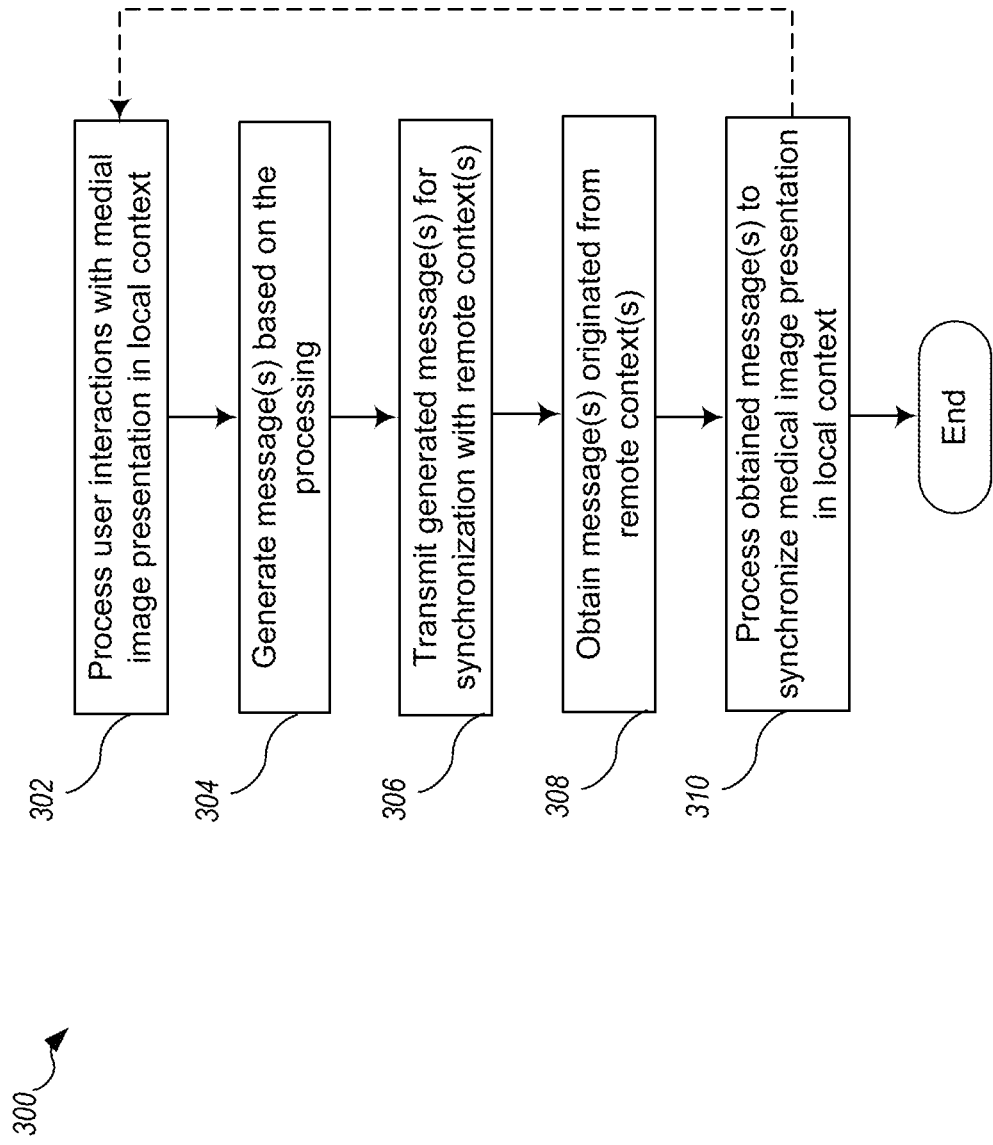
FIG. 3 is a flow diagram of an example process that illustrates the function of the presently disclosed technology, according to some embodiments.

FIG. 3 is a flow diagram of an example method 300 implemented in accordance with some embodiments. Illustratively, at least some part of the method 300 can be performed by the medical image processing and display system 104, and in some embodiments, with the medical image acquisition system 102. Some part of the method 300 can also be performed, or partially performed, by other software applications on the computing device 400 or performed, or partially performed, on elements such as switches and routers that play a part in transmitting information between computers and other electronic devices. The method 300 starts at block 302, where the method 300 includes processing user interactions with medical image presentation in a local context. Illustratively, the user interactions can originate from an input device such as a mouse or a keyboard. The user interactions can be performed to adjust the environmental characteristics of the local context. For example, the user may want to change the aspect ratio of the medical image in the local context or insert annotative texts to describe the medical image. The user interactions can be processed with the medical image processing and display system 104, or the medical image acquisition system 102, or other software applications on the computing device 400. Based on the input from user interactions, the environmental characteristics of the local context can be adjusted accordingly, and the medical image and other elements in the local context can be displayed according to the updated environmental characteristics.

At block 304, the method 300 includes generating one or more messages based on the processing at block 302. In some embodiments, the message includes content to communicate the updated environmental characteristics. The message can also include other information. In some embodiments, the message can be encoded for security or other purposes. In some embodiments, the message can be processed (e.g., being split into packets and encapsulated) so that the message can be transmitted over the Internet based on applicable protocol(s).

At block 306, the method 300 includes transmitting the generated message(s) for synchronization with one or more remote contexts. Illustratively, if the local context and the one or more remote contexts belong to multiple processes of the same software application or multiple software applications running on the same device, the transmission of the message can be completed by pure software means. For example, the transmission of the message can be achieved by writing upon and reading from a shared memory accessible by both the local context and the one or more remote contexts. Alternatively or in addition, the transmission of the message can be achieved by implementing a message passing module, via which a process can broadcast and receive messages.

If the local context and the remote context(s) belong to multiple processes running on multiple devices connected by a local network or to the Internet, the transmission of the message can be achieved by both software means and hardware implementations. On the software side, certain Internet protocols, such as TCP, UDP, IP, or the like, can be implemented to ensure the reliable transmission of information. Hardware implementation can include networking devices such as servers, routers, network switches, bridges, and/or modems (e.g., DSL modem, cable modem), etc.

At block 308, the method 300 includes obtaining one or more messages originated from the remote context(s). The message(s) obtained may or may not be responsive to the message(s) transmitted from the local context, at block 306. In some embodiments, the message(s) are decapsulated and concatenated, so that the original content regarding the remote context(s) are restored. In some embodiments, the message(s) are decoded for security or other purposes.

At block 310, the method 300 includes processing the obtained message(s) to synchronize the presentation of the medical image(s) in the local context. In some embodiments, updated environmental characteristics or other information about the remote context(s) is retrieved from the message(s). The presentation of the medical image(s) in the local context can be adjusted accordingly. For example, if the message indicates that the aspect ratio of the medical image(s) in a remote context is changed from 1:1 to 1:0.9, the aspect ratio of the medical image(s) in the local context can be updated accordingly. If the message indicates that annotative labels, shapes, or texts have been added to a remote context, the annotations can be displayed in the local context accordingly. In some embodiments, the local context and the remote context(s) are synchronized in a way that the presentation of the medical images in the contexts are consistent. In some embodiments, if the message is successfully obtained and processed, an acknowledgement is sent back to the remote context where the message is originated; if the message cannot be successfully obtained or processed, a report of error is sent back to the remote context.

Figure 4:
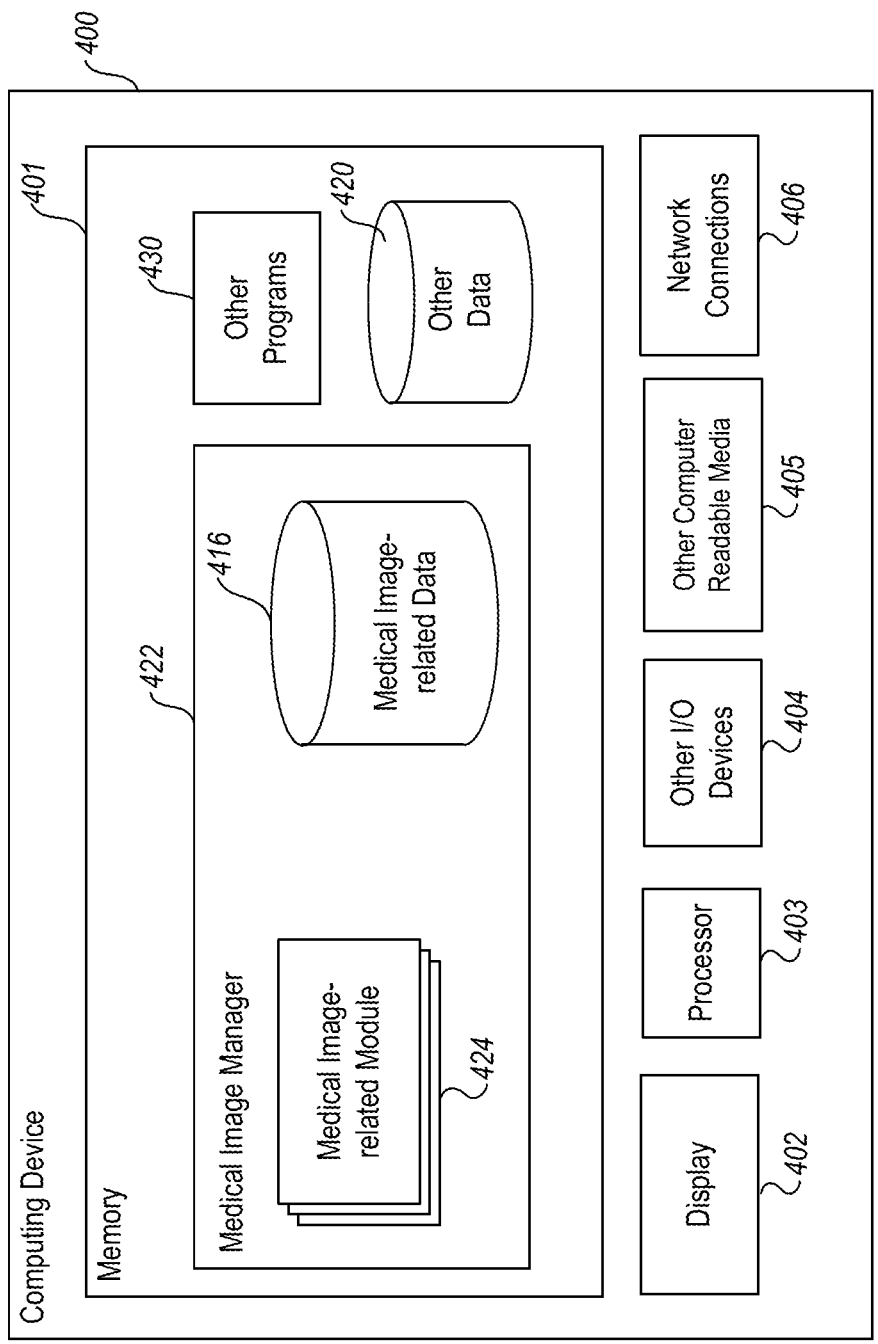
FIG. 4 is a block diagram illustrating elements of an example computing device utilized in accordance with at least some embodiments of the techniques described herein.

FIG. 4 is a block diagram illustrating elements of an example computing device 400 utilized in accordance with at least some embodiments of the techniques described herein. Illustratively, the computing device 400 corresponds to an image processing and display operator's system 144, a medical image capturing operator's system 128, or at least a part thereof.

In some embodiments, one or more general purpose or special purpose computing systems or devices may be used to implement the computing device 400. In addition, in some embodiments, the computing device 400 may comprise one or more distinct computing systems or devices, and may span distributed locations. Furthermore, each block shown in FIG. 4 may represent one or more such blocks as appropriate to a specific embodiment or may be combined with other blocks. Also, the medical image manager 422 may be implemented in software, hardware, firmware, or in some combination to achieve the capabilities described herein.

As shown, the computing device 400 comprises a non-transitory computer memory ("memory") 401, a display 402 (including, but not limited to a light emitting diode (LED) panel, cathode ray tube (CRT) display, liquid crystal display (LCD), touch screen display, projector, etc.), one or more CPUs, GPUs, or other processors 403, Input/Output ("I/O") devices 404 (e.g., keyboard, mouse, RF or infrared receiver, universal serial bus (USB) ports, High-Definition Multimedia Interface (HDMI) ports, other communication ports, and the like), other computer-readable media 405, and network connections 406. The medical image manager 422 is shown residing in memory 401. In other embodiments, some portion of the contents and some, or all, of the components of the medical image manager 422 may be stored on or transmitted over the other computer-readable media 405. The components of the computing device 400 and medical image manager 422 can execute on one or more processors 403 and implement applicable functions described herein. In some embodiments, the medical image manager 422 may operate as, be part of, or work in conjunction or cooperation with other software applications stored in memory 401 or on various other computing devices. In some embodiments, the medical image manager 422 also facilitates communication with peripheral devices via the I/O devices 404, or with another device or system via the network connections 406.

The one or more medical image-related modules 424 is configured to perform actions related, directly or indirectly, to medical image capturing, augmentation, annotation, association, linking, filtering, synchronizing, rendering, presentation, or other manipulations. In some embodiments, the medical image-related module(s) 424 stores, retrieves, or otherwise accesses at least some medical image-related data on some portion of the medical image-related data storage 416 or other data storage internal or external to the computing device 400.

Other code or programs 430 (e.g., further data processing modules, a program guide manager module, a Web server, and the like), and potentially other data repositories, such as data repository 420 for storing other data, may also reside in the memory 401, and can execute on one or more processors 403. Of note, one or more of the components in FIG. 4 may or may not be present in any specific implementation. For example, some embodiments may not provide other computer readable media 405 or a display 402.

In some embodiments, the computing device 400 and medical image-related manager 422 include API(s) that provides programmatic access to add, remove, or change one or more functions of the computing device 400. In some embodiments, components/modules of the computing device 400 and medical image-related manager 422 are implemented using standard programming techniques. For example, the medical image-related manager 222 may be implemented as an executable running on the processor(s) 403, along with one or more static or dynamic libraries. In other embodiments, the computing device 400 and medical image-related manager 422 may be implemented as instructions processed by a virtual machine that executes as one of the other programs 430. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), or declarative (e.g., SQL, Prolog, and the like).

In a software or firmware implementation, instructions stored in a memory configure, when executed, one or more processors of the computing device 400 to perform the functions of the medical image-related manager 422. In some embodiments, instructions cause the processor(s) 403 or some other processor, such as an I/O controller/processor, to perform at least some functions described herein.

The embodiments described above may also use well-known or other synchronous or asynchronous client-server computing techniques. However, the various components may be implemented using more monolithic programming techniques as well, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs or other processors. Some embodiments may execute concurrently and asynchronously, and communicate using message passing techniques. Equivalent synchronous embodiments are also supported by a medical image-related manager 422 implementation. Also, other functions could be implemented or performed by each component/module, and in different orders, and by different components/modules, yet still achieve the functions of the computing device 400 and medical image-related manager 422.

In addition, programming interfaces to the data stored as part of the computing device 400 and medical image-related manager 422, can be available by standard mechanisms such as through C, C++, C#, and Java APIs; libraries for accessing files, databases, or other data repositories; scripting languages such as XML; or Web servers, FTP servers, NFS file servers, or other types of servers providing access to stored data. The medical image-related data storage 416 and data repository 420 may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, and Web Services (XML-RPC, JAX-RPC, SOAP, and the like). Other variations are possible. Other functionality could also be provided by each component/module, or existing functionality could be distributed amongst the components/modules in different ways, yet still achieve the functions of the medical image-related manager 422.

Furthermore, in some embodiments, some or all of the components of the computing device 400 and medical image-related manager 422 may be implemented or provided in other manners, such as at least partially in firmware or hardware, including, but not limited to one or more application-specific integrated circuits ("ASICs"), standard integrated circuits, controllers (e.g., by executing appropriate instructions, and including microcontrollers or embedded controllers), field-programmable gate arrays ("FPGAs"), complex programmable logic devices ("CPLDs"), and the like. Some or all of the system components or data structures may also be stored as contents (e.g., as executable or other machine-readable software instructions or structured data) on a computer-readable medium (e.g., as a hard disk; a memory; a computer network, cellular wireless network or other data transmission medium; or a portable media article to be read by an appropriate drive or via an appropriate connection, such as a DVD or flash memory device) so as to enable or configure the computer-readable medium or one or more associated computing systems or devices to execute or otherwise use, or provide the contents to perform, at least some of the described techniques.

The various embodiments described above can be combined to provide further embodiments. All of the U.S. patents, U.S. patent application publications, U.S. patent applications, foreign patents, foreign patent applications and non-patent publications referred to in this specification or listed in the Application Data Sheet are incorporated herein by reference, in their entirety. In cases where the present patent application conflicts with an application or other document incorporated herein by reference, the present application controls. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for presenting medical images in a plurality of contexts, the method comprising:
   processing user interactions with a presentation of one or more first medical images of a subject organ or tissue in a local context, wherein the one or more first medical images reflect a view of the subject organ or tissue from a first perspective and captured at a first time;

generating a message based, at least in part, on processing the user interactions;

transmitting the message for synchronization with one or more remote contexts, wherein one or more second medical images of the subject organ or tissue are presented in the one or more remote contexts and wherein the one or more second medical images reflect a view of the subject organ or tissue from a second perspective and captured at a second time;

obtaining one or more messages originated from the one or more remote contexts; and processing the obtained one or more messages to synchronize the presentation of the one or more first medical images in the local context in accordance with the first and second perspectives and the first and second times, so that changes of the subject organ or tissue over time are presented consistently.

2. The method of claim 1, wherein the local context includes at least one of a Web browser, tab, frame, or window for displaying information on a display device.

3. The method of claim 1, wherein the one or more messages are obtained responsive to the transmitted message for synchronization.

4. The method of claim 1, wherein the message includes attributes of annotative element(s) applied to the presentation of the one or more medical images in the local context.

5. The method of claim 4, wherein the annotative elements include at least one of a label, shape, or text.

6. The method of claim 1, wherein processing the obtained one or more messages to synchronize the presentation of the one or more first medical images in the local context in accordance with the first and second perspectives and the first and second times comprises automatically reflecting one or more annotative elements consistently between the one or more second medical images presented in the one or more remote contexts and the one or more first medical images presented in the local context.

7. A non-transitory computer-readable medium storing contents that, when executed by one or more processors, cause the one or more processors to perform actions comprising:

processing user interactions with a presentation of one or more first medical images of a subject organ or tissue in a local context, wherein the one or more first medical images reflect a view of the subject organ or tissue from a first perspective and captured at a first time;

generating a message based, at least in part, on processing the user interactions;

transmitting the message for synchronization with one or more remote contexts, wherein one or more second medical images of the subject organ or tissue are presented in the one or more remote contexts and wherein the one or more second medical images reflect a view of the subject organ or tissue from a second perspective and captured at a second time;

obtaining one or more messages originated from the one or more remote contexts; and processing the obtained one or more messages to synchronize the presentation of the one or more first medical images in the local context in accordance with the first and second perspectives and the first and second times, so that changes of the subject organ or tissue over time are presented consistently.

8. The computer-readable medium of claim 7, wherein the local context includes at least one of a Web browser, tab, frame, or window for displaying information on a display device.

9. The computer-readable medium of claim 7, wherein the one or more messages are obtained responsive to the transmitted message for synchronization.

10. The computer-readable medium of claim 7, wherein the message includes attributes of annotative element(s) applied to the presentation of the one or more medical images in the local context.

11. The computer-readable medium of claim 10, wherein the annotative elements include at least one of a label, shape, or text.

12. A system, comprising:

one or more processors; and memory storing contents that, when executed by the one or more processors, cause the system to perform actions comprising:

processing user interactions with a presentation of one or more first medical images of a subject organ or tissue in a local context, wherein the one or more first medical images reflect a view of the subject organ or tissue from a first perspective and captured at a first time;

generating a message based, at least in part, on processing the user interactions;

transmitting the message for synchronization with one or more remote contexts, wherein one or more second medical images of the subject organ or tissue are presented in the one or more remote contexts and wherein the one or more second medical images reflect a view of the subject organ or tissue from a second perspective and captured at a second time;

obtaining one or more messages originated from the one or more remote contexts; and processing the obtained one or more messages to synchronize the presentation of the one or more first medical images in the local context in accordance with the first and second perspectives and the first and second times, so that changes of the subject organ or tissue over time are presented consistently.

13. The system of claim 12, wherein the local context includes at least one of a Web browser, tab, frame, or window for displaying information on a display device.

14. The system of claim 12, wherein the one or more messages are obtained responsive to the transmitted message for synchronization.

15. The system of claim 12, wherein the message includes attributes of annotative element(s) applied to the presentation of the one or more medical images in the local context.

16. The system of claim 15, wherein the annotative elements include at least one of a label, shape, or text.

* * * * *